(12) United States Patent
Uchiyama

(10) Patent No.: US 11,524,109 B2
(45) Date of Patent: Dec. 13, 2022

(54) DRUG SOLUTION ADMINISTRATION DEVICE AND METHOD FOR CONTROLLING DRUG SOLUTION ADMINISTRATION DEVICE

(71) Applicant: TERUMO KABUSHIKI KAISHA, Tokyo (JP)

(72) Inventor: Joji Uchiyama, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 356 days.

(21) Appl. No.: 16/366,999

(22) Filed: Mar. 27, 2019

(65) Prior Publication Data

US 2019/0217008 A1 Jul. 18, 2019

Related U.S. Application Data

(63) Continuation of application No. PCT/JP2017/034164, filed on Sep. 21, 2017.

(30) Foreign Application Priority Data

Oct. 5, 2016 (JP) .............................. JP2016-197536

(51) Int. Cl.
*A61M 5/142* (2006.01)
*A61M 5/172* (2006.01)
*A61M 5/145* (2006.01)

(52) U.S. Cl.
CPC ........ *A61M 5/14248* (2013.01); *A61M 5/142* (2013.01); *A61M 5/145* (2013.01);
(Continued)

(58) Field of Classification Search
CPC .............. A61M 5/14248; A61M 5/142; A61M 5/14244; A61M 5/145; A61M 5/1452;
(Continued)

(56) References Cited

U.S. PATENT DOCUMENTS

2004/0059316 A1 3/2004 Smedegaard
2010/0262078 A1* 10/2010 Blomquist .......... A61M 5/1452
604/151
(Continued)

FOREIGN PATENT DOCUMENTS

CN 101970031 A 2/2011
CN 104043159 A 9/2014
(Continued)

OTHER PUBLICATIONS

Written Opinion in International Application No. PCT/JP2017/034164 dated Dec. 26, 2017 (10 pages).
(Continued)

*Primary Examiner* — Emily L Schmidt
*Assistant Examiner* — Antarius S Daniel
(74) *Attorney, Agent, or Firm* — Foley & Lardner LLP

(57) ABSTRACT

A drug solution administration device includes: an injection unit configured to inject a drug solution in vivo; a container; a push-out mechanism configured to allow the drug solution stored inside the container to flow into the injection unit; a sealing member attached to the push-out mechanism and pressed against a wall surface of the containing space; a drive mechanism configured to generate a drive force for moving the push-out mechanism back and forth; and a control unit is configured such that, when a predetermined time has passed after the control unit controls the drive mechanism to stop operation of the drive mechanism, the control unit controls the drive mechanism to move the push-out mechanism and to shift a position of the sealing member relative to the wall surface of the containing space.

3 Claims, 7 Drawing Sheets

(52) U.S. Cl.
CPC .......... *A61M 5/1452* (2013.01); *A61M 5/172* (2013.01); *A61M 2005/14252* (2013.01); *A61M 2005/14268* (2013.01); *A61M 2205/8206* (2013.01)

(58) Field of Classification Search
CPC .. A61M 5/168; A61M 5/172; A61M 5/14216; A61M 5/1454; A61M 5/14546; A61M 5/14566; A61M 5/16809; A61M 2005/14252; A61M 2005/14268; A61M 2005/14573; A61M 2205/14
See application file for complete search history.

(56) References Cited

U.S. PATENT DOCUMENTS

| | | |
|---|---|---|
| 2014/0330206 A1 | 11/2014 | Moore |
| 2015/0122338 A1 | 5/2015 | Hunter et al. |
| 2015/0157788 A1* | 6/2015 | Gescheit ........... A61M 5/14244 604/67 |

FOREIGN PATENT DOCUMENTS

| | | |
|---|---|---|
| JP | 2002-136594 A | 5/2002 |
| JP | 2013-000207 A | 1/2013 |
| JP | 2014-533599 A | 12/2014 |
| JP | 2016-022145 A | 2/2016 |
| WO | WO-2011/122574 A1 | 10/2011 |
| WO | WO-2016/075976 A1 | 5/2016 |
| WO | WO-2016/132936 A1 | 8/2016 |

OTHER PUBLICATIONS

Extended European Search Report dated Apr. 1, 2020 in corresponding European Patent Application No. 17858217.7.
Office Action dated Dec. 11, 2020 in corresponding Chinese Patent Application No. 201780058906.0.
International Searching Authority, "International Search Report," issued in connection with International Patent Application No. PCT/JP2017/034164, dated Dec. 26, 2017.
International Searching Authority, "Written Opinion," issued in connection with International Patent Application No. PCT/JP2017/034164, dated Dec. 26, 2017.

* cited by examiner

DRUG SOLUTION ADMINISTRATION DEVICE AND METHOD FOR CONTROLLING DRUG SOLUTION ADMINISTRATION DEVICE

CROSS-REFERENCE TO RELATED APPLICATIONS

This is a bypass continuation of PCT Application No. PCT/JP2017/034164, filed on Sep. 21, 2017, which claims priority to Japanese Application No. 2016-197536, filed on Oct. 5, 2016. The contents of these applications are hereby incorporated by reference in their entireties.

BACKGROUND

The present disclosure relates to a drug solution administration device used for in vivo administration of a drug solution and relates to a method for controlling a drug solution administration device.

In the related art, as a device for administering a drug solution such as insulin, there is known a portable administration device that enables continuous administration of a drug solution while being attached to the skin of a patient of interest or a subject.

In this drug solution administration device, a cylindrical body (such as a syringe) and a plunger form a space that contains a drug solution. Moving the plunger inside the cylinder pushes out the drug solution inside the cylinder and introduces the drug solution in vivo through a tube or the like connected to the cylinder (refer to JP 2002-136594 A).

SUMMARY

In the drug solution administration device disclosed in JP 2002-136594 A, a seal (a sealing member) such as rubber is provided in a portion of the plunger that is to be brought into contact with the cylindrical body, or at a leading end of the plunger, in order to inhibit leakage of the drug solution from a base end of the cylindrical body. However, when a liquid feed is stopped and the seal is left to stand for a long time, the seal may stick to an inner wall of the cylinder and cause difficulty in moving the plunger when the liquid feed is resumed. Alternatively, sticking of the seal may be erroneously detected as clogging in a flow path of the drug solution. Furthermore, when the sticking is resolved, an accumulated pressing force acts on the plunger at once, which may cause an unintended quantity of liquid feed.

An object of certain embodiments of the present invention is to provide a drug solution administration device that inhibits a push-out mechanism such as a plunger that pushes out a drug solution from having trouble moving relative to a container such as a cylindrical body, and relates to a method for controlling a drug solution administration device.

According to one embodiment, a drug solution administration device includes: an injection unit that injects a drug solution in vivo; a container provided with a containing space communicated with the injection unit and configured to contain the drug solution that is to be fed to the injection unit; a push-out mechanism at least a part of which moves back and forth inside the containing space and that allows the drug solution stored inside the containing space to flow into the injection unit; a sealing member attached to the push-out mechanism and pressed against a wall surface of the containing space to inhibit leakage of the drug solution inside the containing space from the push-out mechanism; a drive mechanism that generates a drive force for moving the push-out mechanism back and forth; and a control unit that commands the drive mechanism to start an operation and to stop the operation. When a predetermined time has passed after the command to stop the operation of the drive mechanism, the control unit controls the drive mechanism to move the push-out mechanism and to shift a position of the sealing member relative to the wall surface of the containing space.

According to another embodiment, a method for controlling a drug solution administration device includes: a container provided with a containing space that contains a drug solution; a sealing member pressed against a wall surface of the containing space to inhibit leakage of the drug solution inside the containing space; a drive mechanism that generates a drive force for moving the sealing member back and forth; and a control unit that commands the drive mechanism to start an operation and to stop the operation. When a predetermined time has passed after the command to stop the operation of the drive mechanism, the control unit controls the drive mechanism to move the sealing member and to shift a position of the sealing member relative to the wall surface of the containing space.

According to the drug solution administration device and the method for controlling a drug solution administration device of certain embodiments, when a predetermined time has passed after a command to stop an operation of a drive mechanism, the drive mechanism is commanded to shift a position of a sealing member relative to a wall surface of a containing space. Accordingly, it is possible to inhibit the sealing member from sticking to an inner wall of a container and to inhibit troubles such as difficulty in moving the push-out mechanism, an erroneous detection of clogging, and an unintended quantity of liquid feed.

BRIEF DESCRIPTION OF THE DRAWINGS

FIG. 4(A) illustrates a state before introducing a cannula in vivo, while FIG. 4(B) illustrates a state after introducing the cannula in vivo with a puncture tool. FIG. 4(C) illustrates a state in which the puncture tool is removed and the cannula stays in vivo.

FIG. 7(A) illustrates a state before connecting the injection unit and a liquid-feed unit, while FIG. 7(B) illustrates a state after connecting the injection unit and the liquid-feed unit.

DETAILED DESCRIPTION

Hereinafter, embodiments of the present invention will be described with reference to the accompanying drawings. Note that the following description does not limit the technical scope or the term meanings recited in the claims. Furthermore, dimensional ratios of the drawings are exaggerated for illustration purpose and may differ from actual ratios.

With reference to FIG. 1 to FIG. 9, a drug solution administration device according to a first embodiment will now be described in detail. FIG. 1 to FIG. 8 are views for describing an arrangement of each unit of the drug solution administration device according to this embodiment.

The drug solution administration device according to the present embodiment is a portable insulin administration device 100 that feeds insulin as a drug solution in a diabetic patient or a user in vivo. Hereinafter, the drug solution administration device is described as the insulin administration device 100.

Figure 1:
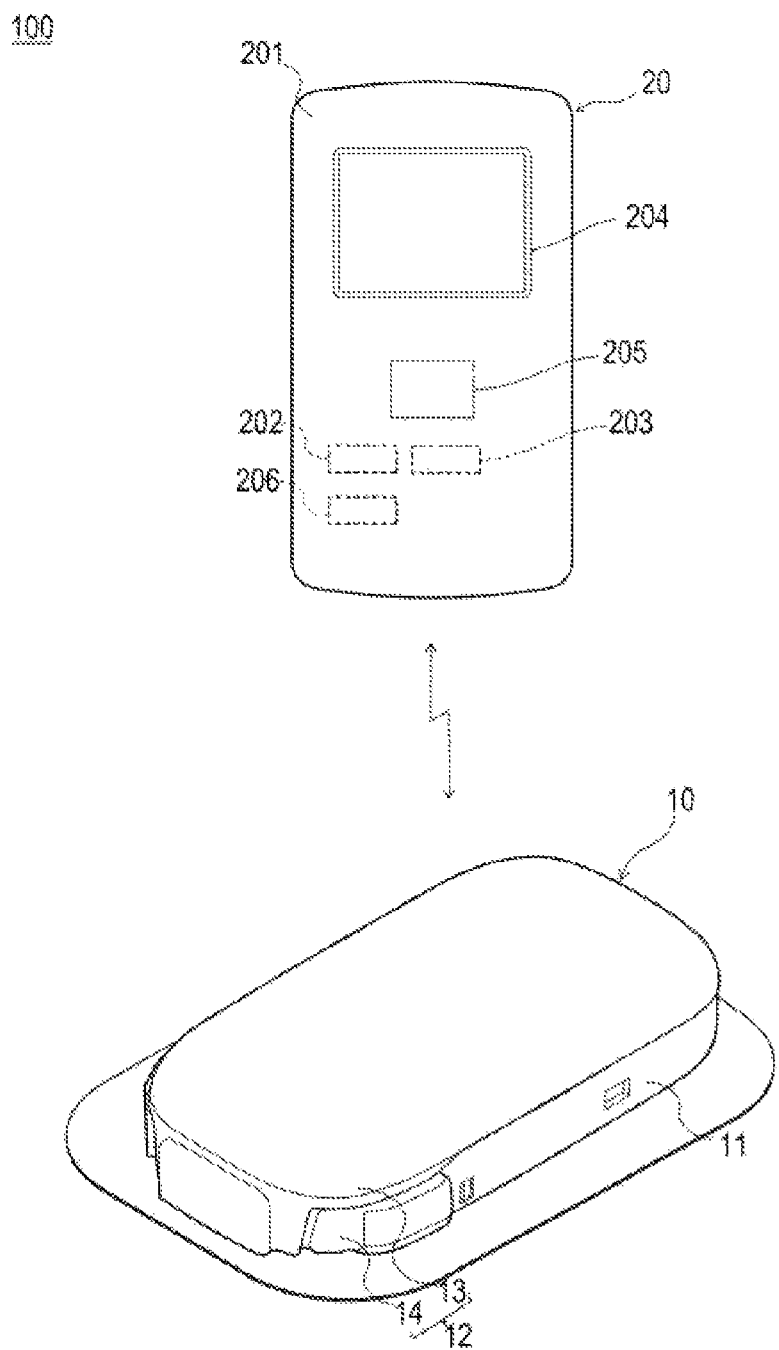
FIG. 1 is a schematic view of a drug solution administration device according to an embodiment of the present invention.

As illustrated in FIG. 1, the insulin administration device 100 includes a liquid-feed body 10 and a remote controller 20. The liquid-feed body 10 feeds insulin or a drug solution in vivo. The remote controller 20 instructs the liquid-feed body 10 to perform various operations. An arrangement of each unit of the insulin administration device 100 will now be described in detail.

Figure 2:
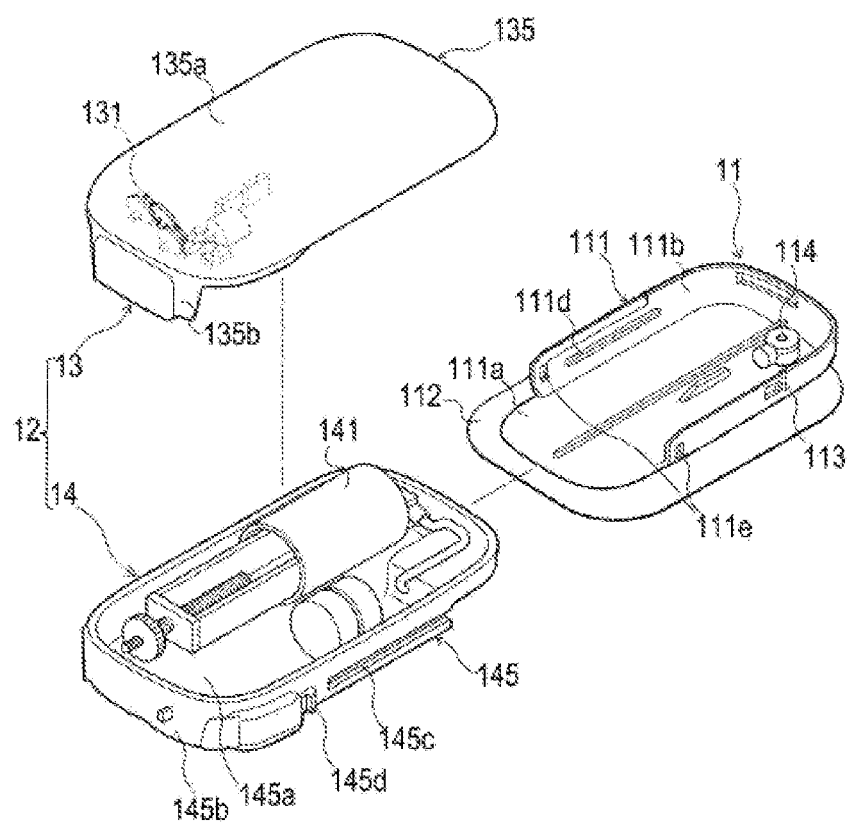
FIG. 2 is an exploded perspective view of a liquid-feed body of the drug solution administration device.
Figure 3:
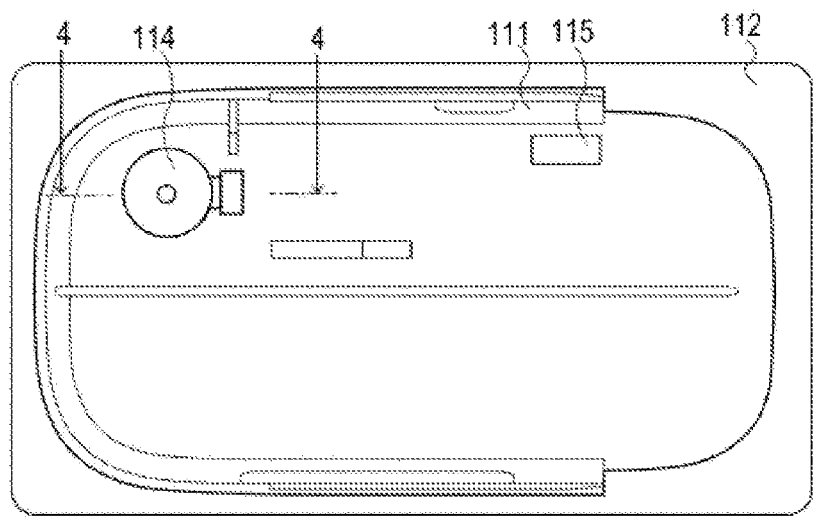
FIG. 3 is a plan view of an injection unit of the drug solution administration device.

As illustrated in FIG. 2, the liquid-feed body 10 includes an injection unit 11 and a liquid-feed unit 12. The injection unit 11 to be attached to a user in vivo is provided with, for example, a cannula 113 that stays in the user in vivo. The liquid-feed unit 12 is provided with a reusable liquid-feed unit 13 and a disposable liquid-feed unit 14. The reusable liquid-feed unit 13 includes, for example, a drive mechanism 131 that generates a drive force to drive members necessary for a liquid feed. The disposable liquid-feed unit 14 includes, for example, a drug solution storage unit 141 filled with insulin and a push-out mechanism 143, to be described, which is used for feeding the drug solution filled in the drug solution storage unit 141.

The injection unit 11 and the liquid-feed unit 12 are configured to be connected to and/or separated from each other. For example, when the user takes a bath, while keeping the injection unit 11 attached in vivo, the user separates the liquid-feed unit 12 that includes the drug solution storage unit 141 filled with insulin and electrical and mechanical structures from the injection unit 11. This operation inhibits warming of the insulin inside the drug solution storage unit 141 and inhibits adhesion of liquid to the electrical and mechanical structures inside the liquid-feed unit 12 so as not to make the structures wet.

Furthermore, the reusable liquid-feed unit 13 and the disposable liquid-feed unit 14 are configured to be connected to and/or separated from each other. After a predetermined period of time, when the insulin or the like inside the drug solution storage unit 141 is used up, the reusable liquid-feed unit 13 and the disposable liquid-feed unit 14 may be separated, and the disposable liquid-feed unit 14 may be disposed of and changed to a new one. On the other hand, the reusable liquid-feed unit 13 is provided with relatively expensive components that are changed less frequently than those mounted on the disposable liquid-feed unit 14. For example, a motor 136 and a gear group 137 to be described are mounted on the reusable liquid-feed unit 13. In this manner, components that are to be discarded after use for a predetermined period and components that are relatively expensive are mounted on different housings. Mounting the relatively expensive components on the reusable liquid-feed unit 13 for reuse enables reduction of manufacturing costs of the device and costs associated with use. Each arrangement will now be described.

First, the injection unit 11 will be described. As illustrated in FIG. 2, for example, the injection unit 11 includes an injection body 111 (also referred to as "cradle"), a stick-on unit 112, the cannula 113, a support 114, and a magnet 115 (see FIG. 3). The stick-on unit 112 allows the injection body 111 to stick to the user in vivo. The cannula 113 protrudes from the injection body 111 and is to stay in vivo. The support 114 is mounted on the injection body 111 and supports the cannula 113. The magnet 115 is used to detect connection between the injection unit 11 and the liquid-feed unit 12.

Figure 4A:
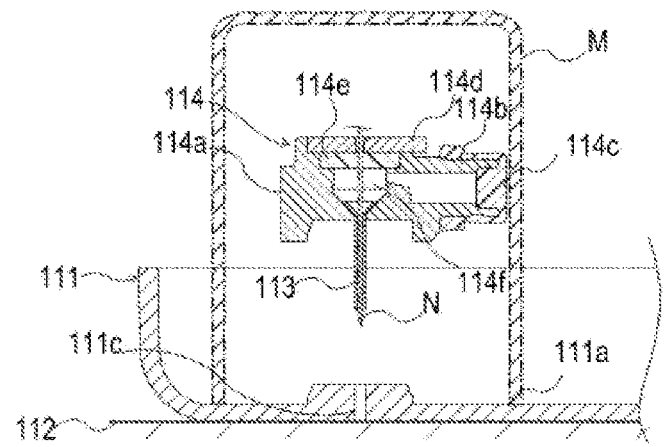
FIGS. 4(A)-4(C) illustrate enlarged sectional views taken along line 4-4 of FIG. 3.
Figure 4B:
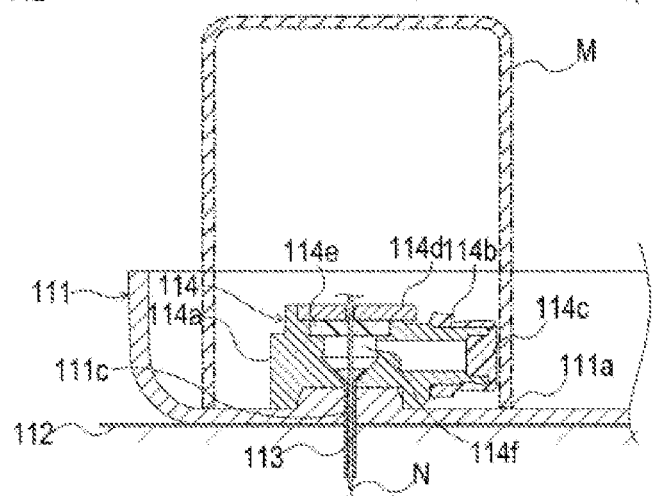
Figure 4C:
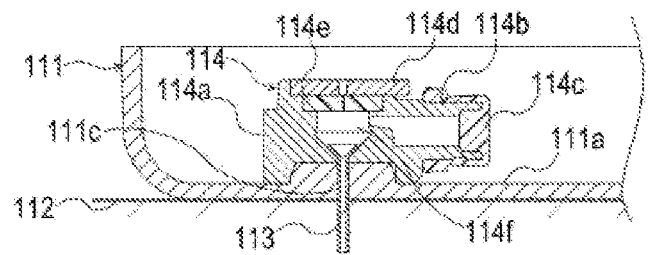

As illustrated in FIG. 2, the injection body 111 includes a flat plate-shaped placement portion 111a and a vertical wall 111b formed by standing a part of the peripheral edge of the placement portion 111a. As illustrated in FIGS. 4(A) to 4(C), the placement portion 111a is provided with an insertion hole 111c that enables insertion of the cannula 113.

Furthermore, as illustrated in FIG. 2, the vertical wall 111b is provided with a protrusion 111d protruding toward the opposite surface and a through-hole 111e as engagement units that maintain a mechanical connection with a second housing 145 of the disposable liquid-feed unit 14 that is to be described. Sliding the second housing 145 of the disposable liquid-feed unit 14 relative to the injection body 111 to connect the second housing 145 to the injection body 111 causes the protrusion 111d to fit in a slot 145c formed outside the second housing 145. In addition, a hook 145d formed in the second housing 145 is caught in the through-hole 111e. Note that the shapes of the engagement units are not limited to the above example as long as the injection body 111 and the second housing 145 of the disposable liquid-feed unit 14 are configured to be connected to and/or separated from each other.

As illustrated in FIG. 3 and FIGS. 4(A) to 4(C), the stick-on unit 112 includes a substantially rectangular sheet-like member. In the placement portion 111a of the injection body 111 of the stick-on unit 112, adhesion is provided to a surface where the vertical wall 111b stands up and to the opposite surface. Taking advantage of the adhesiveness, the stick-on unit 112 enables the injection unit 11 to stick to the user in vivo. Note that the adhesive surface of the stick-on unit 112 that is to be attached in vivo may employ, for example, detachable release paper that covers and protects the stick-on unit 112 so as to inhibit inadvertent sticking of the stick-on unit 112.

The cannula 113 is inserted in vivo and used for in vivo introduction of the drug solution such as insulin from the drug solution storage unit 141. As illustrated in FIG. 4(A), the cannula 113 includes a cylindrical portion and a truncated conical portion continuously formed on the cylindrical portion. The cylindrical portion and the truncated conical portion are provided with an inner cavity that enables a flow of insulin. With such a shape, the cannula 113 is shaped like a funnel. It is a matter of course that the shape of the cannula 113 is not limited to the above example as long as the cannula 113 enables in vivo introduction of the drug solution from the drug solution storage unit 141.

As illustrated in FIGS. 4(A)-4(C), the support 114 includes a bottom 114a, a connection port 114b, a cap 114c, a lid 114d, and a seal 114e. The bottom 114a supports the cannula 113. The connection port 114*b* includes an inner cavity into which a liquid-feed tube 142 (see FIGS. 7(A) and 7(B)) of the disposable liquid-feed unit 14 is inserted. The cap 114*c* is to be attached to the connection port 114*b* to cover the connection port 114*b*. The lid 114*d* is attached to an upper surface of the bottom 114*a* (a surface opposite to a surface of the bottom 114*a* that is placed on the injection body 111). The seal 114*e* is provided between the bottom 114*a* and the lid 114*d*.

The bottom 114*a* is a base of the support 114, having a substantially cylindrical shape in this embodiment. As illustrated in FIG. 4(C), for example, the bottom 114*a* includes an internal space 114*f* in which the cannula 113 is placed. The internal space 114*f* is shaped like a funnel according to the shape of the cannula 113 and supports the cannula 113.

In the bottom 114*a*, as illustrated in FIG. 4(A), for example, the connection port 114*b* extends in a direction intersecting with an axis of the cylindrical portion included in the cannula 113. The inner cavity of the connection port 114*b* is communicated with the internal space 114*f* of the bottom 114*a*.

It is preferred that the cap 114*c* should enable insertion of the liquid-feed tube 142 of the disposable liquid-feed unit 14 to be described and that the cap 114*c* should include a material that keeps the liquid-feed tube 142 and the connection port 114*b* in a liquid-tight manner. An example of such a material includes rubber.

As illustrated in FIG. 4(C), the lid 114*d* has a function of pressing the seal 114*e*. The lid 114*d* is provided with a through-hole that is coaxial with an axial direction of the cannula 113 and that enables insertion of a needle N of a puncture tool M to be described.

The seal 114*e* is configured to be punctured with the needle N of the puncture tool M and is configured to inhibit insulin from leaking out of the through-hole of the lid 114*d* after the puncture tool M is removed. An example of the material of the seal 114*e* includes rubber. The puncture tool M in each of FIGS. 4(A) and 4(B) is illustrated simply.

The cannula 113 stays in vivo by the puncture tool M provided with, for example, the needle N that is to be inserted into the inner cavity of the cannula 113 supported by the support 114, and a biasing member (not illustrated) that applies a biasing force to the support 114 and the needle N in a direction in which the needle N and the cannula 113 protrude from the placement portion 111*a*.

Specifically, first, a user attaches the injection body 111 to his/her body surface with the stick-on unit 112. Next, the user inserts the needle N from the through-hole formed in the lid 114*d* of the support 114 and attaches the support 114 to the puncture tool M to insert the needle N through the inner cavity of the cannula 113. Next, as illustrated in FIG. 4(A), the user attaches the puncture tool M to the placement portion 111*a*. Next, as illustrated in FIG. 4(B), due to the biasing force of the biasing member included in the puncture tool M, the support 114 and the needle N are injected in the direction in which the needle N and the cannula 113 protrude from the placement portion 111*a*. The support 114 herein is fixed to the placement portion 111*a* by a latching mechanism (not illustrated). Next, as illustrated in FIG. 4(C), while attaching the support 114 to the placement portion 111*a*, the user detaches the puncture tool M including the needle N from the placement portion 111*a*. Accordingly, the cannula 113 stays in vivo. Note that the puncture tool M to which the support 114 is attached may be stored while being attached to the injection body 111, and the puncture tool M may be independently detached after being fixed by the latching mechanism of the support 114.

Herein, the cannula 113 and the support 114 correspond to a circulation unit provided with a first flow path that allows a flow of the drug solution.

The magnet 115 is used to detect connection between the liquid-feed unit 12 and the injection unit 11 when the liquid-feed unit 12 is fitted in the injection unit 11. As described later, the disposable liquid-feed unit 14 included in the liquid-feed unit 12 is provided with a fitting detection unit 139 used for detecting fitting between the liquid-feed unit 12 and the injection unit 11 together with the magnet 115. In this embodiment, the fitting detection unit 139 includes a reed switch and is placed in a first housing 135 of the reusable liquid-feed unit 13 to be described. The reed switch is arranged above the magnet 115 when the liquid-feed unit 12 is attached to the injection unit 11. In the reed switch, metal plates are provided inside a glass tube, being separated from each other. When the magnet 115 is arranged above or close to the reed switch, the metal plates come into contact with each other. The fitting detection unit 139 is electrically connected to a first control unit 134 to be described. Accordingly, the fitting detection unit 139 detects whether the liquid-feed unit 12 is attached to the injection unit 11 by detecting contact between the metal plates of the fitting detection unit 139. The fitting detection unit 139 is not limited to the above arrangement as long as the fitting detection unit 139 is configured to detect whether the liquid-feed unit 12 is fitted in the injection unit 11. For example, a push type switch may be appropriately employed as the fitting detection unit 139.

Figure 5:
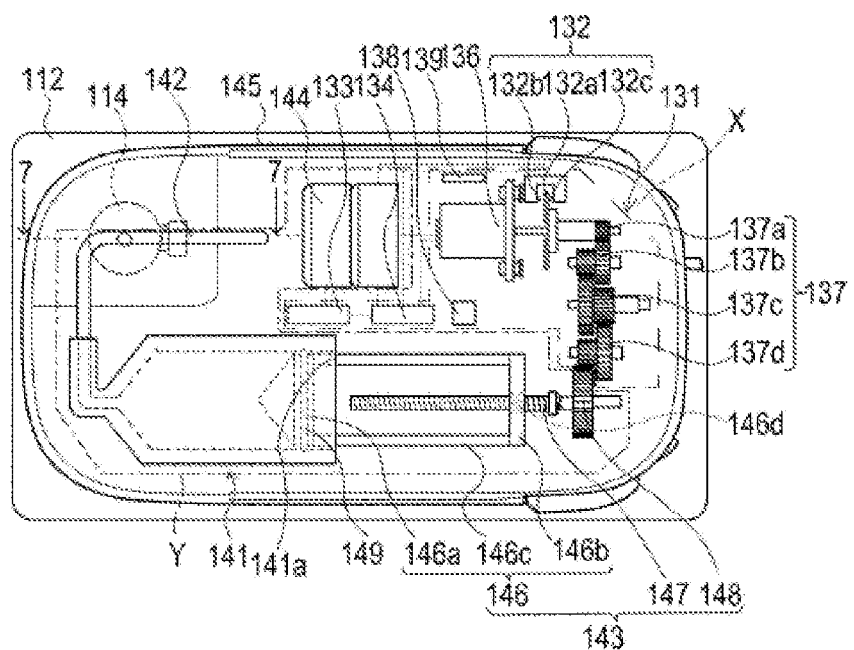
FIG. 5 is a schematic plan view illustrating a structure of each unit in the liquid-feed body of the drug solution administration device according to the embodiment.

Next, the reusable liquid-feed unit 13 will be described. As illustrated in FIGS. 2 and 5, the reusable liquid-feed unit 13 includes the drive mechanism 131, a rotation detection unit 132, a first communication unit 133, the first control unit 134, the first housing 135, and the fitting detection unit 139. The drive mechanism 131 drives members necessary for a liquid feed. The rotation detection unit 132 detects rotation of the drive mechanism 131. The first communication unit 133 communicates with the remote controller 20. The first control unit 134 controls, for example, the drive mechanism 131 and the first communication unit 133. The first housing 135 holds these members. The fitting detection unit 139 is used to detect fitting of the liquid-feed unit 12 with respect to the injection unit 11. In FIG. 5, a section surrounded by the dotted line X represents components to be attached to the reusable liquid-feed unit 13, and a section surrounded by the dot-and-dash line Y represents components to be attached to the disposable liquid-feed unit 14. Furthermore, FIG. 5 does not illustrate the first housing 135, for simplicity.

As illustrated in FIG. 5, for example, the drive mechanism 131 includes the motor 136 and the gear group 137. The motor 136 is provided with an output shaft that causes rotation by electric power from a battery 144 of the disposable liquid-feed unit 14. The gear group 137 reduces the speed of rotation caused by the motor 136 and transmits the rotation to the push-out mechanism 143 of the disposable liquid-feed unit 14.

In the output shaft, the motor 136 generates a drive force, as rotational motion, necessary for moving a slide 146 of the push-out mechanism 143. A stepping motor is employed as the motor 136 in this embodiment. Stepping motors are preferable from a viewpoint of safeness and the like, because stepping motors stop rotation at the time of a short circuit. A specific aspect of the motor 136 is not limited to the above example as long as the motor 136 is configured to generate a drive force by rotation and has a size mountable on the portable insulin administration device 100. Besides a stepping motor, the motor 136 may be, for example, a DC motor or an AC motor.

The gear group 137 is used to transmit the power of rotation generated from the motor 136 to the push-out mechanism 143 that presses the drug solution storage unit 141. As illustrated in FIG. 5, the gear group 137 includes a first gear 137a connected to the motor 136, and a second, a third, and a fourth gear 137b, 137c, and 137d that mesh with adjacent gears.

The first gear 137a is provided with one kind of teeth that meshes with adjacent gears. In regard to the second, third, and fourth gears 137b, 137c, and 137d, two kinds of teeth that mesh with adjacent gears are arranged in an axial direction in which the gears rotate.

The second gear 137b is arranged adjacent to the first gear 137a and the third gear 137c in a direction intersecting with a rotating shaft of the first gear 137a (vertical direction in FIG. 5).

The third gear 137c is arranged adjacent to the second gear 137b and the fourth gear 137d in the direction intersecting with the rotating shaft of the first gear 137a (vertical direction in FIG. 5).

The fourth gear 137d is arranged adjacent to the third gear 137c and a fifth gear 148 of the disposable liquid-feed unit 14 in the direction intersecting with the rotating shaft of the first gear 137a (vertical direction in FIG. 5).

The gear group 137 and the fifth gear 148 include spur gears. The number of gears and the like are not limited to the above example as long as the power generated by the rotation of the motor 136 is transmitted to the push-out mechanism 143. Furthermore, in the gear group 137 and the fifth gear 148, the number of gears and teeth or the like are set in such a manner that torque from the motor 136 is reduced to a preset value. However, specifications such as the number of gears and teeth are not limited to the above example as long as a desired reduction gear ratio is achieved within a given space. Still further, in this embodiment, rotational directions of an input gear corresponding to the first gear 137a and an output gear corresponding to the fifth gear 148 may be the same or different. A material and arrangement of the gear group 137 are not particularly limited as long as the gear group 137 enables transmission of an output from the output shaft 136 of the motor 136 to the push-out mechanism 143. Examples of the material include metals and resin materials such as plastic.

The motor 136 is connected to the first gear 137a of the gear group 137 through a coil spring (not illustrated).

As illustrated in FIG. 5, the rotation detection unit 132 includes an optical sensor provided with a blocking member 132a arranged in a portion of the first gear 137a close to the motor 136, and a light emitting unit 132b and a light receiving unit 132c that face each other across the blocking member 132a.

Figure 6:
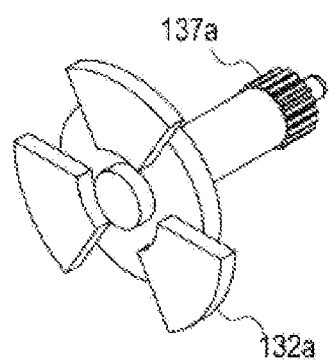
FIG. 6 is a perspective view illustrating a blocking member included in a rotation detection unit that detects rotation of a motor included in a drive mechanism.

As illustrated in FIG. 6, the blocking member 132a is provided with a plurality of substantially sector forms similar to blades of an electric fan at an interval of a certain angle in a circumferential direction of the first gear 137a. When detection light emitted from the light emitting unit 132b of the optical sensor passes through portions without the blades of the blocking member 132a, the light receiving unit 132c receives the detection light. Conversely, when the detection light from the light emitting unit 132b is blocked by the blades of the blocking member 132a, the light receiving unit 132c does not receive the detection light. Because the blades of the blocking member 132a are provided at a regular interval, the number of rotations of the output shaft of the motor 136 is detected based on a time interval (frequency) at which the detection light is received. Because a reduction gear ratio obtained by the gear group 137 and the fifth gear 148 and a pitch of a feed screw 147 of the push-out mechanism 143 are fixed (not variable), a quantity of drug-solution feed is calculated by detecting the number of rotations of the output shaft 136 of the motor 136.

Although the blocking member 132a is provided with three fan-shaped blades in FIG. 6, for example, the shape and the number of the blades are not limited to those illustrated in FIG. 6 as long as the blades switch between blocking and passing of the detection light. In this embodiment, the rotation detection unit 132 detects the number of rotations of the output shaft of the motor 136 to obtain a quantity of liquid feed, but a method of detecting a quantity of liquid feed is not limited thereto. For example, a quantity of liquid feed may also be obtained by a control signal sent to the motor 136. Although the optical sensor is used herein for detecting the number of rotations, the present invention is not limited to the optical sensor as long as the number of rotations of the motor is detected. Besides the optical sensor, the present invention may employ, for example, a magnetic sensor.

The first communication unit 133 includes electronic devices necessary for communication with the remote controller 20. As described later, the remote controller 20 is provided with a second communication unit 202 that transmits and receives information to and from the first communication unit 133 of the reusable liquid-feed unit 13, using Bluetooth® Low Energy (BLE) communication or short-range wireless communication.

Figure 8:
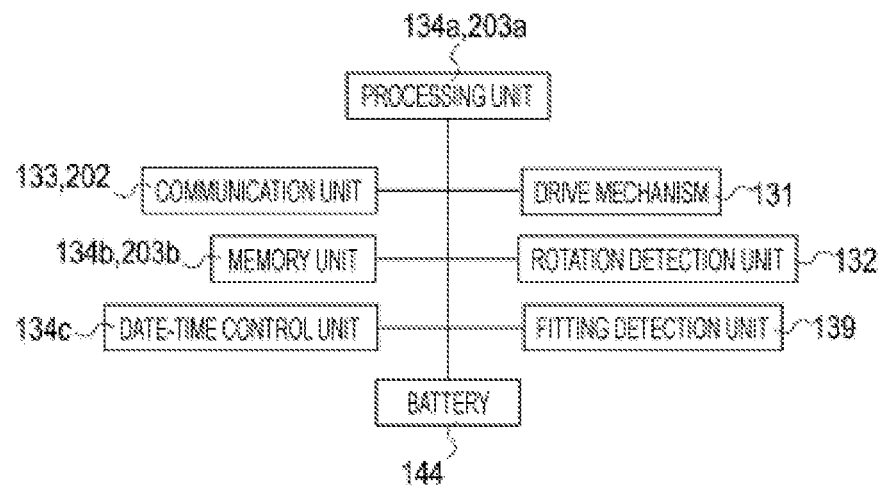
FIG. 8 is a block diagram illustrating an arrangement of a control system in the drug solution administration device.

As illustrated in FIG. 8, the first control unit 134 includes a processing unit 134a (corresponding to a control unit), a memory unit 134b, and a date-time control unit 134c. The first control unit 134 includes a known microcomputer and controls the whole components that operate in the liquid-feed unit 12.

The processing unit 134a performs arithmetic operations and commands necessary for operations of, for example, the motor 136, the first communication unit 133, and the rotation detection unit 132 included in the drive mechanism 131. As one of the commands, the processing unit 134a commands the motor 136 included in the drive mechanism 131 to start rotation of a liquid feed and to stop the rotation. The processing unit 134a includes, for example, a CPU.

The memory unit 134b stores, for example, an output of the number of rotations of the motor 136 from the rotation detection unit 132, instructions for the motor 136 to start rotation or to stop the rotation and the time of the instructions, and stores information associated with attachment and detachment between the liquid-feed unit 12 and the injection unit 11. The memory unit 134b includes, for example, a RAM and a ROM.

The date-time control unit 134c is used when time information is required, for example, in recording the time when the number of rotations of the motor 136 is detected and the time when the motor 136 is instructed to start rotation or to stop the rotation. The date-time control unit 134c includes, for example, a real time clock.

As illustrated in FIG. 2, the first housing 135 includes an upper surface 135a and a side wall 135b. The upper surface 135a covers components such as the drive mechanism 131, the rotation detection unit 132, the first communication unit 133, and the first control unit 134. The side wall 135b is formed by standing a part of the peripheral edge of the upper surface 135a. To the upper surface 135a, for example, the drive mechanism 131, the rotation detection unit 132, the first communication unit 133, and the first control unit 134 are attached operatively.

In addition, the first housing 135 includes a projection (not illustrated) that projects inward from an inner surface of the side wall 135b and that allows the reusable liquid-feed unit 13 to be connected to and/or separated from the disposable liquid-feed unit 14. In this embodiment, the first housing 135 is a component including resin such as plastic, but the present invention is not limited thereto as long as the first housing 135 has a certain degree of strength and the like. Because the fitting detection unit 139 is described in the description of the magnet 115 of the injection unit 11, details of the fitting detection unit 139 will be omitted here.

Next, the disposable liquid-feed unit 14 will be described. As illustrated in FIG. 5, the disposable liquid-feed unit 14 includes the drug solution storage unit 141 (corresponding to a container), the liquid-feed tube 142, the push-out mechanism 143, the battery 144, and the second housing 145. The drug solution storage unit 141 is filled with insulin. The liquid-feed tube 142 communicates the inner cavity of the connection port 114b provided in the injection unit 11 and the drug solution storage unit 141. The push-out mechanism 143 is mechanically connected to the drive mechanism 131 to push out the insulin inside the drug solution storage unit 141 to the liquid-feed tube 142. The battery 144 supplies electric power to, for example, the drive mechanism 131. The second housing 145 holds these members.

The drug solution storage unit 141 has a cylindrical shape. The liquid-feed tube 142 is connected to one end of the drug solution storage unit 141. The other end of the drug solution storage unit 141 is provided with an opening 141a. The slide 146 of the push-out mechanism 143 to be described is inserted into the drug solution storage unit 141 from the opening 141a, and insulin is stored in a space partitioned by the drug solution storage unit 141 and the slide 146.

Figure 7A:
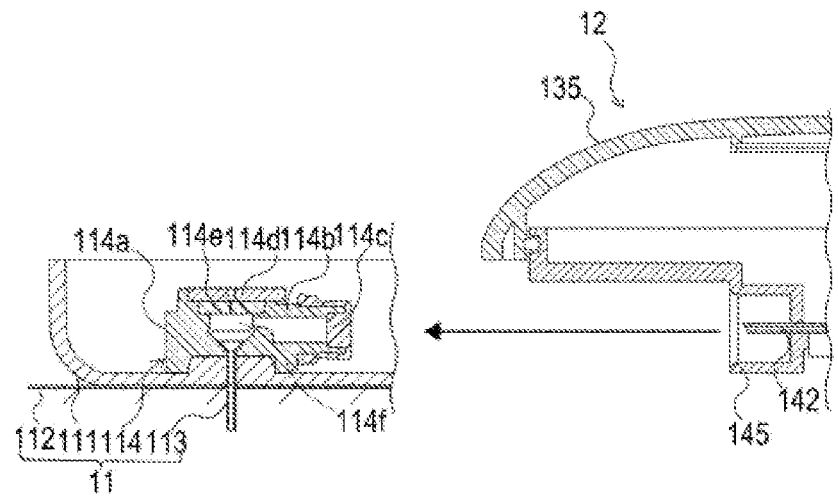
FIGS. 7(A) and 7(B) illustrate cross-sectional views taken along line 7-7 of FIG. 5.
Figure 7B:
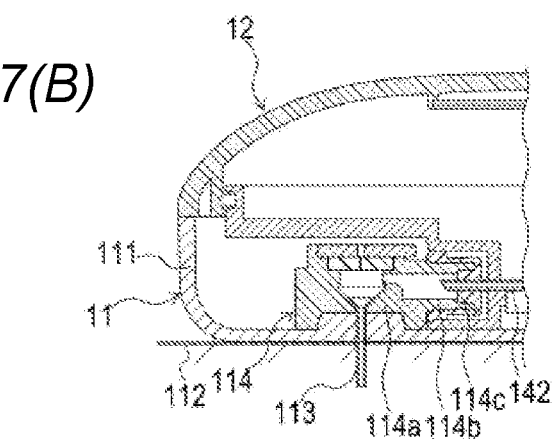

As illustrated in FIGS. 7(A) and 7(B), in this embodiment, the liquid-feed tube 142 includes a metallic thin tube having a sharp leading end. When the liquid-feed unit 12 is slid and fitted in the injection unit 11 as illustrated in FIG. 7(A), the sharp leading end of the liquid-feed tube 142 penetrates through the cap 114c of the injection unit 11 as illustrated in FIG. 7(B), being inserted into and connected to the inner cavity of the connection port 114b. The liquid-feed tube 142 is communicated with the internal space of the support 114 and the cannula 113. Furthermore, the liquid-feed tube 142 is connectable and/or separable from the support 114 and the cannula 113, corresponding to a circulation unit provided with a second flow path that allows a flow of the drug solution from the drug solution storage unit 141.

As illustrated in FIG. 5, the push-out mechanism 143 includes the slide 146, the feed screw 147, and the fifth gear 148. The slide 146 moves back and forth inside the internal space of the drug solution storage unit 141. The feed screw 147 engages with a female screw 146d formed in the slide 146 and moves the slide 146 back and forth. The fifth gear 148 meshes with the fourth gear 137d of the drive mechanism 131 and is to be connected to the feed screw 147.

As illustrated in FIG. 5, the slide 146 includes a push-out member 146a, a feed plate 146b, and a connecting plate 146c. The push-out member 146a moves back and forth inside the drug solution storage unit 141 while maintaining sealing performance so that the drug solution does not leak toward the slide 146. The feed plate 146b is provided with the female screw 146d that meshes with the feed screw 147. The connecting plate 146c connects the push-out member 146a and the feed plate 146b.

The push-out member 146a is inserted through the opening 141a of the drug solution storage unit 141 and forms a space that contains the drug solution in the internal space of the drug solution storage unit 141. The sealing member 149 is attached to an outer surface of the push-out member 146a, and in order not to allow leakage of the drug solution from between the push-out member 146a and a cylindrical inner wall of the drug solution storage unit 141, the sealing member 149 is fitted in the cylindrical inner wall and moves back and forth in the horizontal direction of FIG. 5 along the inner wall. The containing space (internal space of the drug solution storage unit 141) that contains the drug solution changes in size (volume) depending on the position of the push-out member 146a in the drug solution storage unit 141. The push-out member 146a is also referred to as a plunger or a pusher. The sealing member 149 is also referred to as a seal. In this embodiment, the sealing member 149 is formed into an O-ring, but the present invention is not limited thereto as long as the sealing member 149 enables inhibition of leakage of the drug solution inside the drug solution storage unit 141 from the push-out member 146a.

The feed plate 146b having a plate shape is provided with a hole. This hole is provided with the female screw 146d that meshes with a male screw of the feed screw 147.

The connecting plate 146c connects the push-out member 146a and the feed plate 146b with two plates. However, the shape of the connecting plate 146c is not limited to this example as long as the connecting plate 146c connects the push-out member 146a and the feed plate 146b together and causes those members to move in an integrated manner. Besides this example, the connecting plate 146c may have a hollow form that is fitted, for example, in the cylindrical inner wall of the drug solution storage unit 141 in the entire circumference.

The feed screw 147 has a typical male screw shape, and a part of the feed screw 147 meshes with the female screw 146d of the feed plate 146b. The head of the feed screw 147 is provided with, for example, a cross-shaped slot that meshes with a part of the fifth gear 148 to be described.

The fifth gear 148 is arranged at a position where the fifth gear 148 meshes with the fourth gear 137d while the reusable liquid-feed unit 13 and the disposable liquid-feed unit 14 are connected to each other in the second housing 145.

The fifth gear 148 includes, as illustrated in FIG. 5, gear teeth and a bit that meshes (engages) with the slot on the head of the feed screw 147. The bit is provided at an end of a rotating shaft or the center of rotation of the gear.

The bit of the fifth gear 148 is similar in shape to a leading end of a driver (also referred to as a screwdriver or a turnscrew) that fastens a typical screw. With such an arrangement, the bit of the fifth gear 148 meshes with the recessed slot on the head of the feed screw 147 and transmits power caused by rotation of the fifth gear 148.

Because the teeth and the rotating shaft of the fifth gear 148 are similar in shape to known ones, this embodiment will not give a description of their shapes.

The feed screw 147 and the fifth gear 148 are rotatably attached to the second housing 145.

When the fifth gear 148 rotates along with rotation of the fourth gear 137d included in the drive mechanism 131, the feed screw 147 rotates. The feed plate 146b is restricted from rotating in a rotational direction of the feed screw 147, and along with the rotation of the feed screw 147, the feed plate 146b moves along a spiral axis of the male screw of the feed screw 147. The push-out member 146a connected to the feed plate 146b through the connecting plate 146c moves inside the drug solution storage unit 141 along with the movement of the feed plate 146b. Movement of the push-out member 146a in a direction in which the push-out member 146a is pushed into the drug solution storage unit 141 (a direction in which the volume of the containing space decreases) causes the insulin inside the containing space formed by the drug solution storage unit 141 and the push-out member 146a to be fed to the liquid-feed tube 142.

When the reusable liquid-feed unit 13 and the disposable liquid-feed unit 14 are connected to each other, the battery 144 is electrically connected to the motor 136, the rotation detection unit 132, the first communication unit 133, and the first control unit 134 in the reusable liquid-feed unit 13 and supplies electric power to each unit. In this embodiment, the battery 144 includes two batteries connected in series. Note that the number of batteries and a connection method such as serial or parallel connection are not particularly limited to this example as long as electric power is fed to each unit.

As illustrated in FIG. 2, the second housing 145 includes a bottom surface 145a and a side wall 145b. On the bottom surface 145a, for example, the drug solution storage unit 141, the liquid-feed tube 142, the push-out mechanism 143, and the battery 144 are placed. The side wall 145b is formed by standing the peripheral edge of the bottom surface 145a.

The second housing 145 is configured to be connected to and/or separated from the injection body 111. Specifically, in this embodiment, as illustrated in FIG. 2, the side wall 145b is provided with the slot 145c and the hook 145d. The slot 145c is fitted in the protrusion 111d formed in the injection body 111. The hook 145d is caught in the through-hole 111e formed in the injection body 111. Sliding the second housing 145 into the injection body 111 causes the protrusion 111d of the injection body 111 to fit in the slot 145c of the second housing 145 and causes the hook 145d of the second housing 145 to be caught in the through-hole 111e of the injection body 111. Accordingly, the second housing 145 is connected to the injection body 111.

The second housing 145 includes a recess (not illustrated) that engages with the projection provided on the side wall 135b of the first housing 135. This arrangement enables connection and/or separation of the second housing 145 to and from the first housing 135. Connection between the first housing 135 and the second housing 145 causes the drive mechanism 131 mounted on the first housing 135 to be mechanically connected to the push-out mechanism 143 mounted on the second housing 145. In addition, the motor 136, the rotation detection unit 132, the first communication unit 133, and the first control unit 134 mounted on the first housing 135 are electrically connected to the battery 144 mounted on the second housing 145.

In this embodiment, the second housing 145 is a component including resin such as plastic, but the present invention is not limited thereto, similarly to the first housing 135, as long as the second housing 145 has a certain degree of strength and the like.

Next, the remote controller 20 will be described. As illustrated in FIG. 1, the remote controller 20 includes a remote controller body 201, the second communication unit 202, a second control unit 203, a monitor 204 (corresponding to an alarm unit), a button 205, and a battery 206. The second communication unit 202 enables wireless communication with the first communication unit 133. The second control unit 203 controls the overall insulin administration device 100. The monitor 204 is provided in the remote controller body 201. The button 205 receives instructions from a user. The battery 206 supplies electric power to each unit of the remote controller 20.

The remote controller body 201 has a size that enables the user to hold the remote controller 20 by one hand, and the remote controller body 201 is a relatively light component including resin such as plastic.

The second communication unit 202 includes electronic devices necessary for communication with the first communication unit 133 of the liquid-feed body 10. The second communication unit 202 in this embodiment uses Bluetooth® Low Energy (BLE) communication or technology called short-range wireless communication that enables communication on low electric power. Using such technology, the second communication unit 202 transmits and receives information to and from the liquid-feed body 10. However, a communication method is not limited to BLE as long as the second communication unit 202 enables wireless communication with the liquid-feed body 10.

As illustrated in FIG. 8, the second control unit 203 includes a processing unit 203a and a memory unit 203b. The second control unit 203 includes a known microcomputer and controls the whole components that operate in the remote controller 20. The processing unit 203a performs arithmetic operations and commands necessary for operations of, for example, the second communication unit 202 and the monitor 204. The processing unit 203a includes, for example, a CPU.

The memory unit 203b stores, for example, programs necessary for controlling the second communication unit 202 and the monitor 204. The memory unit 203b includes, for example, a RAM and a ROM. For example, when the memory unit 203b includes a RAM and a ROM, the processing unit 203a reads various programs prestored in the ROM into the RAM and executes the programs and causes operations such as a liquid feed. The monitor 204, the button 205, and the battery 206 are similar to known ones in arrangement. Accordingly, illustration in FIG. 8 and description of those members are omitted here.

Next, exemplary applications of the insulin administration device 100 will be described.

Prior to use of the insulin administration device 100, first, a user fits the injection unit 11 in vivo and places the cannula 113 in vivo, using the puncture tool M as described above.

Furthermore, prior to use of the insulin administration device 100, the user connects the reusable liquid-feed unit 13 and the disposable liquid-feed unit 14 in an integrated manner to form the liquid-feed unit 12. The user then operates the remote controller 20 and instructs priming (first priming) to fill insulin in the liquid-feed tube 142 of the disposable liquid-feed unit 14. Upon reception of the instruction from the remote controller 20, the first control unit 134 causes the drive mechanism 131 to move the slide 146 of the push-out mechanism 143 by a predetermined distance. Accordingly, the insulin contained inside the drug solution storage unit 141 is fed to the liquid-feed tube 142, and the liquid-feed tube 142 is filled with the insulin.

Next, the liquid-feed unit 12 is fitted in the injection unit 11 and both members are connected to each other.

Next, the user operates the remote controller 20 and instructs priming (second priming) to fill the insulin in the inner cavity of the cannula 113.

Next, the user operates the remote controller 20 and feeds the insulin in vivo by selecting liquid-feed mode from, for example, the basal mode in which insulin is constantly fed in a fixed quantity and the bolus mode in which a quantity of insulin fed per unit time is increased temporarily.

Figure 9:
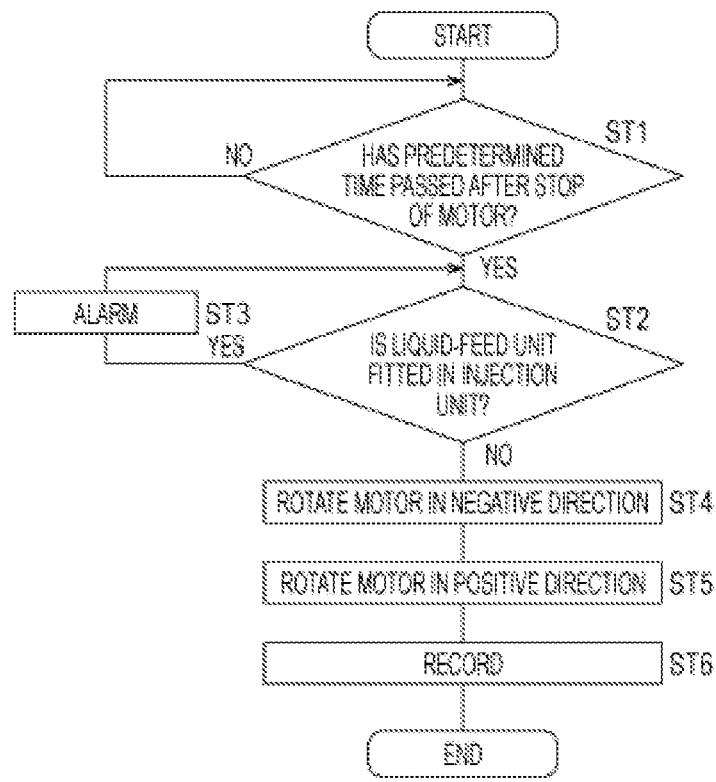
FIG. 9 is a flowchart illustrating movement of a push-out mechanism relative to a drug solution storage unit in order to inhibit sticking in the drug solution administration device according to the embodiment.

Hereinafter described is movement of the push-out mechanism 143 relative to the drug solution storage unit 141 in order to inhibit the sealing member 149 from sticking to the inner wall of the drug solution storage unit 141. FIG. 9 is a flowchart illustrating movement of the push-out mechanism 143 relative to the drug solution storage unit 141 in order to inhibit sticking.

As described above, the memory unit 134b records information associated with, for example, the number of rotations of the motor 136 and a command to start rotation or to stop the rotation of the motor 136. The processing unit 134a refers to the memory unit 134b and determines whether a predetermined time, for example, one hour has passed after the command to stop the rotation of the motor 136 (ST1).

If the sealing member 149 such as an O-ring is kept in close contact with the inner wall of the drug solution storage unit 141 for a long time, the sealing member 149 may stick to the inner wall of the drug solution storage unit 141 due to, for example, adhesiveness of the member. Accordingly, the push-out mechanism 143 with the sealing member 149 attached thereto is required to inhibit the sticking by moving the sealing member 149 relative to the drug solution storage unit 141. When a predetermined time has passed after the command to stop the rotation of the motor 136 (ST1: YES), the processing unit 134a determines whether the injection unit 11 is detached from the liquid-feed unit 12 (ST2). This process is to inhibit the drug solution inside the drug solution storage unit 141 from being fed in vivo by the relative movement of the push-out mechanism 143.

In a case in which the liquid-feed unit 12 is not detached from the injection unit 11 (ST2: YES), the processing unit 134a alerts the user to detach the liquid-feed unit 12 from the injection unit 11 through, for example, the monitor 204 (ST3).

In a case in which the liquid-feed unit 12 is detached from the injection unit 11 (ST2: NO), the processing unit 134a controls the motor 136 to rotate in a direction opposite to a direction of drug-solution feed (ST4). This operation causes the liquid-feed tube 142 to take in air. The processing unit 134a controls the rotation of the motor 136 so that a quantity of air to be taken in (air intake quantity) does not reach a capacity of the drug solution storage unit 141. In other words, the processing unit 134a controls the rotation of the motor 136 so that an air intake quantity is limited to about a volume of the flow path of the liquid-feed tube 142.

The processing unit 134a then rotates the motor 136 in the same direction as the direction of drug-solution feed (ST5). The rotation of the motor 136 herein rotates, for example, to such an extent that the push-out member 146a is moved back to the position before the movement of the push-out member 146a due to rotation of the motor 136 in the negative direction. Accordingly, the sealing member 149 attached to the outer surface of the push-out member 146a moves relative to the inner wall of the drug solution storage unit 141 and is inhibited from sticking to the inner wall.

Upon completion of the rotation of the motor 136, the rotation detection unit 132 detects the end of rotation of the motor 136 and writes the time in the memory unit 134b (ST6). Because the rotation detection unit 132 writes data into the memory unit 134b when the motor 136 operates or stops rotation, it is possible to obtain an elapsed time based on the start-stop time of the motor 136.

Next, effects of this embodiment will be described. In this embodiment, when a predetermined time has passed after the command to stop the operation of the motor 136, the processing unit 134a of the first control unit 134 commands the motor 136 to rotate in the direction opposite to the direction of drug-solution feed, and further, to rotate in the same direction as the direction of drug-solution feed. Such an operation causes a shift in position of the sealing member 149 relative to the drug solution storage unit 141. When the sealing member 149 attached to the push-out member 146a is left standing without moving the push-out member 146a for a predetermined time, the sealing member 149 sticks to the inner wall of the drug solution storage unit 141, which may cause difficulty in resuming the operation of the push-out member 146a afterward. Accordingly, as described above, driving the motor 136 to move the push-out mechanism 143 that includes the push-out member 146a inhibits sticking of the sealing member 149 and avoids difficulty in resuming the operation of the push-out mechanism 143 to which the sealing member 149 is attached.

The injection unit 11 and the liquid-feed unit 12 including the drug solution storage unit 141 are configured to be connected to and/or separated from each other. When a predetermined time has passed after the command to stop the operation of the motor 136 and when the processing unit 134a of the first control unit 134 detects, through the fitting detection unit 139, that the liquid-feed unit 12 is separated from the injection unit 11, the processing unit 134a commands the motor 136 to move the push-out mechanism 143. This command makes it possible to inhibit the drug solution from being fed in vivo when the push-out mechanism 143 is operated to inhibit the sealing member 149 from sticking to the drug solution storage unit 141.

When a predetermined time has passed after the command to stop the operation of the motor 136, the processing unit 134a of the first control unit 134 rotatably drives the motor 136 in the same rotational direction as the direction of drug-solution feed. Accordingly, it is possible to inhibit the sealing member 149 from sticking to the inner wall of the drug solution storage unit 141 without a special operation.

In addition, the processing unit 134a of the first control unit 134 enables reduction of the drug solution discharged from the liquid-feed tube 142 to the outside by rotating the motor 136 in the negative direction before rotating the motor 136 in the positive direction.

Furthermore, the processing unit 134a of the first control unit 134 controls the air intake quantity from the liquid-feed tube 142 that depends on the movement of the push-out member 146a to be equal to or less than the volume of the liquid-feed tube 142. Accordingly, even when the motor 136 is rotated in the negative direction, it is possible to inhibit a fluid such as air from flowing into the internal space of the drug solution storage unit 141.

Note that the present invention is not limited to the aforementioned embodiments and may employ various modifications within the scope of the claims. In the embodiments described above, when a predetermined time has passed after the command to stop the operation of the motor 136, the motor 136 is rotated in the negative direction and the motor 136 is then rotated in the positive direction. However, the present invention is not limited to this example. Besides the above example, the motor 136 may rotate in either direction, positive or negative as long as the sealing member 149 attached to the push-out member 146a moves relative to the drug solution storage unit 141. Furthermore, in the embodiments described above, when the liquid-feed unit 12 is not detached from the injection unit 11, a user is alerted by a display on the monitor 204, but the present invention is not limited to this example. Besides the above example, a user may be alerted by a sound as well as a display. Alternatively, a user may be alerted by a sound independently. Still further, although it depends on a drug solution to be administered, determination of whether the injection unit 11 is detached from the liquid-feed unit 12 (ST2) may be omitted.

The embodiment illustrates the drug solution administration device as a device for administering insulin, but the present invention is not limited thereto. As a drug solution to be administered, the present invention may employ various other drug solutions such as analgesics, anti-cancer drugs, HIV drugs, iron chelating agents, and therapeutic agents for pulmonary hypertension.

REFERENCE NUMERAL LIST

10 LIQUID-FEED BODY
11 INJECTION UNIT
113 CANNULA (CIRCULATION UNIT PROVIDED WITH FIRST FLOW PATH)
114 SUPPORT (CIRCULATION UNIT PROVIDED WITH FIRST FLOW PATH)
12 LIQUID-FEED UNIT
13 REUSABLE LIQUID-FEED UNIT
14 DISPOSABLE LIQUID-FEED UNIT
100 INSULIN ADMINISTRATION DEVICE (DRUG SOLUTION ADMINISTRATION DEVICE)
131 DRIVE MECHANISM
132 ROTATION DETECTION UNIT (DETECTION UNIT)
132a BLOCKING MEMBER
132b LIGHT EMITTING UNIT
132c LIGHT RECEIVING UNIT
134 FIRST CONTROL UNIT
134a PROCESSING UNIT (CONTROL UNIT)
136 MOTOR
139 FITTING DETECTION UNIT
141 DRUG SOLUTION STORAGE UNIT (CONTAINER)
142 LIQUID-FEED TUBE (CIRCULATION UNIT PROVIDED WITH SECOND FLOW PATH)
143 PUSH-OUT MECHANISM
149 SEALING MEMBER

The invention claimed is:

1. A drug solution administration device comprising:
an injection unit configured to inject a drug solution in vivo;
a container comprising a containing space configured to contain the drug solution that is to be fed to the injection unit;
a push-out mechanism, at least a part of which moves back and forth inside the containing space, the push-out mechanism being configured to allow the drug solution stored inside the containing space to flow into the injection unit;
a sealing member attached to the push-out mechanism and pressed against a wall surface of the containing space to inhibit leakage of the drug solution inside the containing space from the push-out mechanism;
a drive mechanism comprising a motor configured to generate a drive force for moving the push-out mechanism back and forth;
a control unit configured to control the drive mechanism to start an operation of the drive mechanism and to stop the operation of the drive mechanism; and
a fitting detection unit configured to detect fitting of the container to the injection unit; and
wherein the injection unit and the container are configured to be connected to and/or separated from each other such that:
when the injection unit is connected to the container, the containing space communicates with the injection unit, and
when the injection unit is separated from the container, the containing space does not communicate with the injection unit;
wherein the control unit is configured such that, when (i) a predetermined time has passed after the control unit controls the drive mechanism to stop the operation of the drive mechanism, and (ii) the fitting detection unit detects separation between the injection unit and the container, the control unit controls the drive mechanism to move the push-out mechanism and to shift a position of the sealing member relative to the wall surface of the containing space by first rotating the motor in a direction opposite to a direction in which the motor is rotated when the drug solution is fed, and, while the injection unit is separated from the container, subsequently rotating the motor in the same direction as the direction in which the motor is rotated when the drug solution is fed to an extent that the push-out mechanism is moved back to an initial position before the movement of the push-out mechanism.

2. The drug solution administration device according to claim 1, wherein:
the injection unit comprises a first flow path that allows the drug solution to flow;
the drug solution administration device further comprises a circulation unit that is arranged between the injection unit and the container and that includes a second flow path communicating with the first flow path; and
the control unit is configured such that, when the motor is rotated in the direction opposite to the direction in which the motor is rotated when the drug solution is fed, the motor is rotated so as to obtain an air intake quantity equal to or less than a volume of the second flow path.

3. A method for controlling a drug solution administration device, the method comprising:
providing a drug solution administration device comprising:
an injection unit configured to inject a drug solution in vivo,
a container comprising a containing space that contains the drug solution,
a push-out mechanism, at least a part of which moves back and forth inside the containing space,
a sealing member pressed against a wall surface of the containing space to inhibit leakage of the drug solution inside the containing space,
a drive mechanism configured to generate a drive force for moving the sealing member back and forth,
a control unit configured to control the drive mechanism to start an operation of the drive mechanism and to stop the operation of the drive mechanism, and
a fitting detection unit configured to detect fitting of the container to the injection unit,
wherein the injection unit and the container are configured to be connected to and/or separated from each other such that:
when the injection unit is connected to the container, the containing space communicates with the injection unit, and
when the injection unit is separated from the container, the containing space does not communicate with the injection unit; and
when (i) a predetermined time has passed after the control unit controls the drive mechanism to stop the operation of the drive mechanism, and (ii) the fitting detection unit detects separation between the injection unit and the container, controlling the drive mechanism to move the push-out mechanism and to shift a position of the sealing member relative to the wall surface of the containing space by first rotating a motor of the drive mechanism in a direction opposite to a direction in which the motor is rotated when the drug solution is fed, and, while the injection unit is separated from the container, subsequently rotating the motor in the same direction as the direction in which the motor is rotated when the drug solution is fed to an extent that the push-out mechanism is moved back to an initial position before the movement of the push-out mechanism.

* * * * *